(12) United States Patent
Van Dalen et al.

(10) Patent No.: US 8,491,123 B2
(45) Date of Patent: Jul. 23, 2013

(54) METHOD AND APPARATUS FOR DETERMINING OCULAR MOTOR FUNCTION

(75) Inventors: Johan T. W. Van Dalen, Tucson, AZ (US); Dan D. Carda, Tucson, AZ (US)

(73) Assignee: Eye Care and Cure Pte. Ltd, Singapore (SG)

( * ) Notice: Subject to any disclaimer, the term of this patent is extended or adjusted under 35 U.S.C. 154(b) by 676 days.

(21) Appl. No.: 12/563,957

(22) Filed: Sep. 21, 2009

(65) Prior Publication Data

US 2011/0069280 A1    Mar. 24, 2011

(51) Int. Cl.
*A61B 3/02* (2006.01)
(52) U.S. Cl.
USPC .......................................... 351/240; 351/244
(58) Field of Classification Search
USPC .................. 351/200, 205, 206, 221, 222, 240, 351/245
See application file for complete search history.

(56) References Cited

U.S. PATENT DOCUMENTS

| | | | |
|---|---|---|---|
| 5,241,332 A * | 8/1993 | Farrell | 351/246 |
| 2009/0219482 A1* | 9/2009 | Van Dalen et al. | 351/201 |
| 2011/0261211 A1* | 10/2011 | Lee et al. | 348/211.4 |

* cited by examiner

*Primary Examiner* — Thomas K Pham
*Assistant Examiner* — Brandi Thomas
(74) *Attorney, Agent, or Firm* — Dale F. Regelman; Quarles & Brady LLP

(57) ABSTRACT

A method and an apparatus are presented for determining ocular motor function in a patient. The patient is instructed to wear a pair of test glasses comprising a first lens having a first color and a second lens having a second color, where the first color and the second color differ. (N) light-emitting devices disposed in a screen are then activated in seriatim, where the (N) light-emitting devices can emit a light comprising the first color and where (N) is greater than 1. (N) images of the screen are synchronously captured upon receiving a signal from the patient indicating an activated light-emitting device is illuminated by a light comprising the second color. Finally, the (N) images are transformed into an ocular motor functioning map.

15 Claims, 7 Drawing Sheets

METHOD AND APPARATUS FOR DETERMINING OCULAR MOTOR FUNCTION

FIELD OF USE

The present invention relates generally to medical devices and more particularly to medical devices for determining ocular motor function.

BACKGROUND

Eye muscle dysfunction (strabismus) that affects horizontal movement of one or both eyes creates an inward or outward deviation, while disorders of the muscles that move the eyes up and down produce a vertical, and occasionally a rotational, ocular muscle imbalance. The ocular misalignment and accompanying double vision (diplopia) may result from direct or indirect damage to one or more of the cranial nerves (III, IV, VI) that innervate a particular extra-ocular muscle or muscle group (paralytic strabismus, as may occur following head trauma); as a consequence of direct involvement to the affected muscle itself (restrictive strabismus, for example in a patient with thyroid eye disease); or as a combination of the two etiologies (an orbital fracture where ocular contents, including muscles, are trapped in the fracture site, accompanied by an eye muscle paralysis of the trapped muscle). It is essential for eye care professionals to perform various tests that identify the involved muscle(s) and the type of deviation present, and quantify the amount of deviation for documentation purposes and to assist in planning a course of treatment.

Several methods exist to test for eye muscle dysfunction. One, the Hess test, utilizes a tangent screen consisting of a gray, wall-mounted board. A grid of coordinate curved horizontal and vertical lines appears as a virtual sphere. The patient is seated 0.5 meters from the screen with their head immobilized by a head/chin rest. Because the test is dependent upon color dissociation, the patient wears goggles of red and green complementary filters, red over the right eye and green over the left.

Another method, the Lancaster Red-Green test, is a variation of the Hess test and has similar components: it consists of a calibrated tangent screen, originally printed or sewn onto a piece of dark gray material. The nine diagnostic positions of gaze are marked on the screen, each 22.5 degrees or 45 prism diopters away from the center. The patient is seated 1 meter from the screen, and the head is similarly immobilized. The test utilizes the same goggles as the Hess test, but both the patient's and examiner's flashlights include a cover with a slit such that the light projected onto the screen is in the shape of a bar.

In older versions of the Hess screen the examiner holds a flashlight that projects a dot of red light onto the screen at the intersection of a coordinate. The patient, wearing the red-green goggles, holds a flashlight that projects a green linear target and subjectively superimposes it on the examiner's red dot. The examiner then moves the projected red dot until all nine (9) diagnostic positions of gaze have been evaluated. Newer electronic models have replaced the examiner's handheld flashlight and incorporated point red lights that randomly illuminate at each coordinate, allowing the examiner to observe the test procedure and document the patient's responses. The test is completed after the colored lenses are worn over each eye so that both right and left visual fields are plotted.

With the Lancaster Red-Green Test, both the red and green targets are linear, and again goggles of red and green complementary filters are worn by the patient, with the red filter worn over the right eye. An examiner must still be present to project one of the flashlights. The patient is asked to superimpose a green line projected from his flashlight onto a red line projected on the test screen from the examiner's flashlight. Again, the examiner moves the projected line of red light until all nine diagnostic positions of gaze have been evaluated. Horizontal, vertical, and torsional deviations can be identified and quantified after the patient's responses are correlated to the examiner's target placement. After the test is completed with the right eye fixating, the flashlights are exchanged and the test repeated so that the left eye assumes fixation.

Both the Hess and Lancaster Red-Green tests are fovea-to-fovea tests: the subjective visual direction of each fovea perceives the image seen through each colored filter, but is visually unaware of the image from the opposing eye. The test responses correspond to the direct projection of each fovea, and therefore correlate with the type of deviation present. A patient with a "crossed eye" (esotropia) will indicate that the images are crossed, while a patient who presents with an outward deviation of the eyes (exotropia), will perceive the images as uncrossed.

Since horizontal deviations are caused by problems affecting lateral movement of one or both eyes, these deviations are best appreciated if the green line from the patient's flashlight is projected so that a vertical line is created, while vertical deviations require the line to be projected in a horizontal fashion. While both the Hess and Lancaster Red-Green tests can be used to identify horizontal and vertical derivations, the presence of torsion, a rotational deviation where objects in the vertical meridian are seen as tilted, is difficult to assess with the Hess test because the two test objects—a dot of red light illuminated on the test screen and a line of green light projected from the flashlight held by the patient—are dissimilar in shape.

To score the Hess test, the examiner records the patient's responses on a paper chart, and then connects the dots, which form inner and outer grids. The inner grid measures deviations of approximately 15 degrees, or 30 prism diopters, the practical fields of eye movements from the primary position when the head is immobilized. The outer grid represents deviations of approximately 30 degrees or 60 prism diopters, when head movement is allowed to accompany the movements of the eyes.

The Lancaster Red-Green test also uses a grid for recording patient responses. A single grid sheet has two separate imprinted images of the test's tangent screen, one above the other, implying fixation with each eye. Responses are plotted on the top grid, as first the right eye fixates and then the bottom grid, for fixation with the left eye.

Once the dots are connected, the resulting grids from each test are interpreted by the examiner to reveal the etiology of the ocular misalignment. The grids from the Hess test implicate the affected eye (indicated by the smaller field), the associated under- and over-action of muscles, and may delineate a paralyzed muscle from a restricted one. With the Lancaster Red-Green test, the interpretation of the resulting grids and measurement of the deviation depends on the distance between the red and green lines, as well as the presence of horizontal, vertical or rotational separation of the lines. The field of greatest separation identifies the affected muscle(s) or the greater deviation created when the eye with a restriction fixates; the displaced direction of the patient's line—horizontal, vertical and/or rotational—indicates which horizontal and/or vertical muscles are involved.

While the Hess and Lancaster Red-Green tests aid in the detection of paretic extraocular muscle palsies and of strabismus, their use has been limited by the need for a physician or technician to record the results on an examination chart. Not only does this add to the cost of administering the test, but it introduces a source of error. Furthermore, for the tests to be accurate, the patient's head must remain in a fixed location such that, inter alia, a sagittal plane of the patient is perpendicular to the screen, requiring the use of a system to immobilize the head via head clamps or head/chin rests. These systems can be uncomfortable and can even invoke anxiety in patients, causing some to forego such tests all together.

SUMMARY

In one implementation, a method is presented for determining ocular motor function in a patient. The patient is instructed to wear a pair of test glasses comprising a first lens having a first color and a second lens having a second color, where the first color and the second color differ. (N) light-emitting devices disposed in a screen are then activated in seriatim, where the (N) light-emitting devices can emit a light comprising the first color and where (N) is greater than 1. (N) images of the screen are synchronously captured upon receiving a signal from the patient indicating an activated light-emitting device is illuminated by a light comprising the second color. Finally, the (N) images are transformed into an ocular motor functioning map.

In another implementation, an article of manufacture is presented comprising a microprocessor and a computer readable medium comprising computer readable program code disposed therein for determining ocular motor function in a patient. The computer readable program code comprises a series of computer readable program steps to effect instructing the patient to wear a pair of test glasses comprising a first lens having a first color and a second lens having a second color, where the first color and the second color differ, activating (N) light-emitting devices disposed in a screen in seriatim, where the (N) light-emitting devices can emit a light comprising the first color and where (N) is greater than 1, and synchronously capturing (N) images of the screen upon receiving a signal from the patient indicating an activated light-emitting device is illuminated by a light comprising the second color. Finally, the computer readable program code comprises a series of computer readable program steps to effect transforming the (N) images into an ocular motor functioning map.

Another implementation, a computer program product encoded in a computer readable medium is presented. The computer program product is useable with a programmable computer processor for determining ocular motor function in a patient and comprises computer readable program code which causes the programmable processor to instruct the patient to wear a pair of test glasses comprising a first lens having a first color and a second lens having a second color, where the first color and the second color differ, activate (N) light-emitting devices disposed in a screen in seriatim, where the (N) light-emitting devices can emit a light comprising the first color and where (N) is greater than 1, and synchronously capture (N) images of the screen upon receiving a signal from the patient indicating an activated light-emitting device is illuminated by a light comprising the second color. Finally, the computer program product comprises computer readable program code which causes the programmable processor to transform the (N) images into an ocular motor functioning map.

BRIEF DESCRIPTION OF THE DRAWINGS

Implementations of the invention will become more apparent from the detailed description set forth below when taken in conjunction with the drawings, in which like elements bear like reference numerals.

DETAILED DESCRIPTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
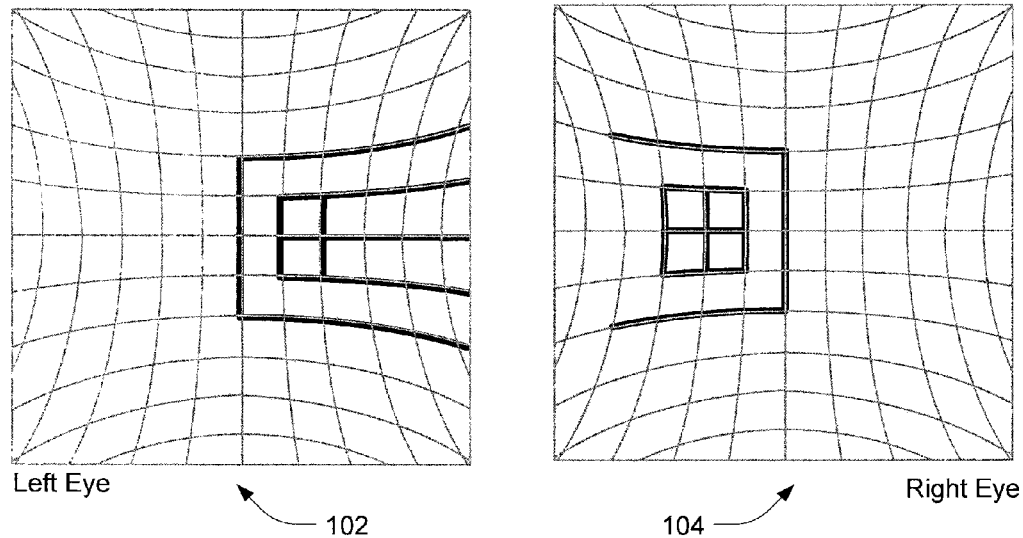
FIG. 1 shows typical chart records of a Hess Screen Test.
Figure 1:
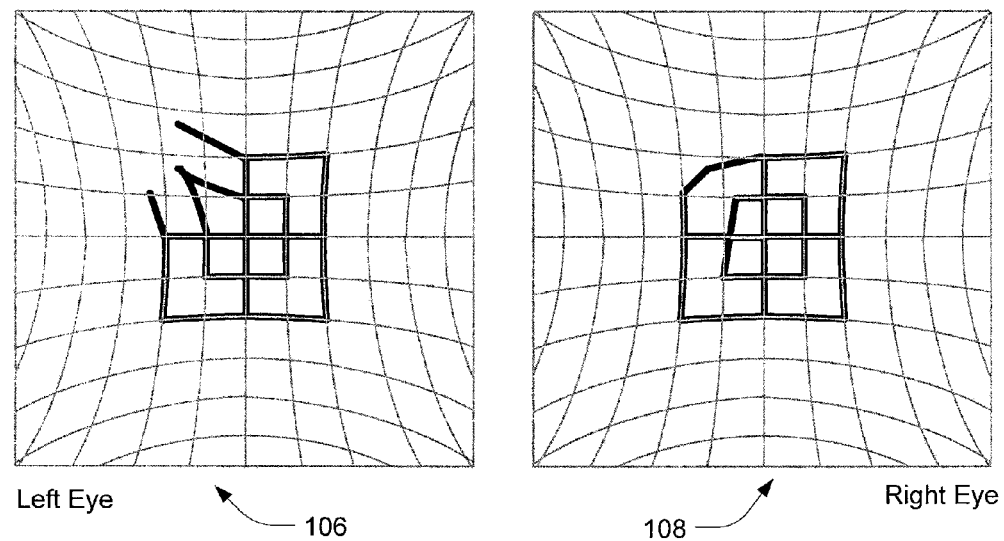

Applicants' invention is illustrated in FIGS. 2A, 2B, 3, 4A, and 4B. For illustrative purposes only, FIGS. 1, 5A, and 5B, are provided depicting the prior art methodology.

Figure 5A:
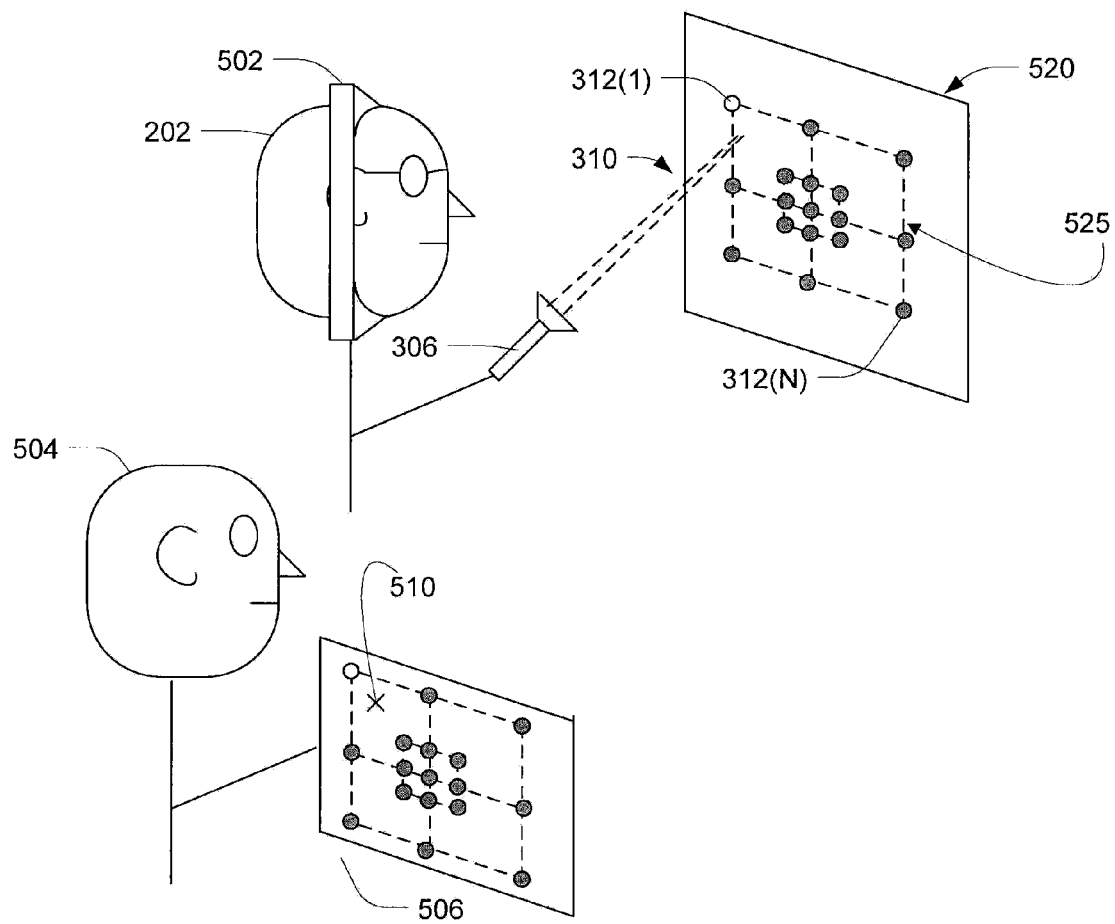
FIG. 5A is a block diagram illustrating a prior art method of performing a Hess Screen Test.
Figure 5B:
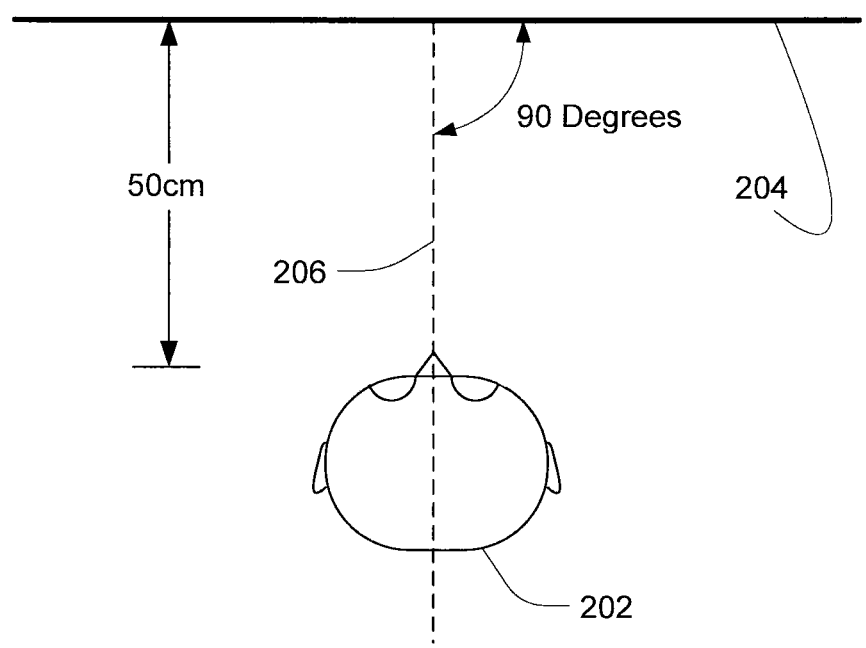
FIG. 5B is a block diagram illustrating a sagittal plane of the patient being perpendicular to the test screen.

Referring now to FIGS. 5A and 5B, the prior art method of performing a Hess Screen Test is presented. A person skilled in the art will understand that the method of performing the Lancaster Red-Green Test is similar to the Hess Screen Test. In the illustrated embodiment of FIG. 5A, patient 202 is shown facing a Hess screen 520. Hess screen 520 is shown as comprising grid 525 which includes (N) fixation points 312, each fixation point being designated in red.

Superimposed on Hess screen 520 is a grid (not illustrated) consisting of horizontally and vertically curved lines produced by projecting the surface coordinates of a sphere onto a surface situated at the same distance of the radius of the sphere. When performing the test, examiner 504 positions patient 202 such that the patient 202's head is at the center of the sphere, frontoparallel to the projected area at a distance of approximately fifty centimeters (50 cm). As can be seen in FIG. 5B this requires that patient 202 is oriented such that nominal vertical plane 206 be perpendicular to screen 520, wherein nominal vertical plane 206 comprises a cranial portion of patient 202's sagittal plane.

Before performing the Hess Screen Test, examiner 504 must neutralize a head tilt or turn by patient 202 by placing patient 202 in the "forced (or controlled) primary position." A small head rotation to a side, and/or or a head tilt upwardly or downwardly may avoid or reduce the symptoms that would otherwise be caused by a paretic muscle by avoiding the field of action of the affected muscle. It may therefore be necessary to immobilize patient 202's head during the examination to achieve valid test results.

In the illustrated embodiment of FIG. 5A, the head of patient 202 is immobilized using head stabilization device 502. In certain embodiments, head stabilization device 502 includes a chin rest and a head rest. In certain embodiments, head stabilization device 502 includes side rests to prevent the head from moving towards either side. In certain embodiments, head stabilization device 502 includes a means for preventing patient 202's head from moving backwardly. In certain embodiments, one or more of the surfaces are adjustable such that a physician or technician can move or lock those surfaces into place to prevent movement of patient 202's head. In certain embodiments, a soft bite bar may be used in addition to or in place of head stabilization device 502. In certain embodiments, head stabilization device 502 is not used and examiner 504 instructs patient 202 not to move patient 202's head.

As illustrated in FIG. 5A, during the Hess test patient 202 wears a pair of glasses typically having one red lens and one green lens. Examiner 504 instructs patient 202 to use a light-emitting device 306 to shine green light 310 onto each of the red fixation points 312 in turn. The use of the colored lenses forces the dissociation of the eyes by filtering what can be seen by each eye. Patient 202 uses the red-lens eye to locate a designated fixation point 312(n), while the green-lens eye cannot see that fixation point. The patient then uses the green-lens eye to direct green light 310 onto the designated fixation point.

As will be clear to one of ordinary skill in the art, during the Hess test, light-emitting device 306 illuminates the circular fixation point with a dot of green light. As will also be clear to one of ordinary skill in the art, if the Lancaster Red-Green test was being performed instead, light emitting device 306 would include a cover or other means to illuminate a linear fixation point with a bar of green light.

After patient 202 has attempted to sequentially direct green light 310 onto each of the fixation points 312, examiner 504 instructs patient 202 to reverse the glasses and to perform the test again.

During the examination, examiner 504 records, by hand, the vertical and horizontal difference in the location of green light 310 and each fixation point 312(n). The record is made on a chart 506 which comprises a copy of grid 525. In the illustrated embodiment of FIG. 5A, the examiner 504 has placed an "X" 510 onto chart 506 to indicate the location that patient 202 directed light 310 when attempting to direct light 310 onto fixation point 312(1). The recorded points are subsequently connected along the horizontally and vertically curved lines to form an inner and outer square. The skew of the resulting squares indicates under- or overaction by an extraocular muscle while the difference in shape of the inner and outer plots indicate the sources of incomitancy.

FIG. 1. presents several exemplary charts created by an examiner, such as examiner 504, during a Hess Screen Test. Charts 102 and 104 are exemplary ocular motor functioning charts for a patient having a paralysis of the sixth nerve. Charts 106 and 108 are exemplary ocular motor functioning charts for a patient having Brown's syndrome in the right eye.

Figure 2A:
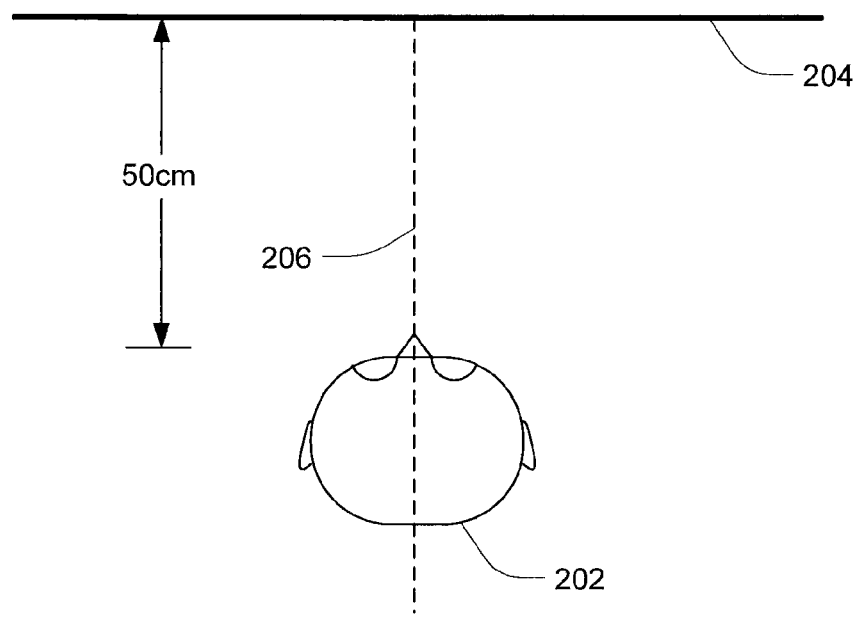
FIG. 2A is a block diagram showing a vertical deviation angle $\Theta$ caused by a rotation of the patient's head.
Figure 2B:
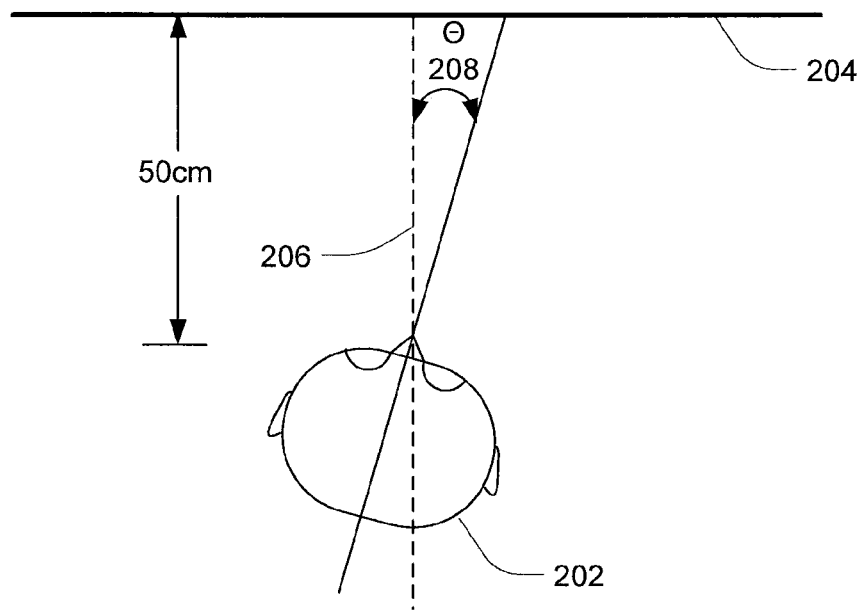
FIG. 2B is a block diagram showing a horizontal deviation angle $\Phi$ caused by an upward tilt of the patient's head.

Turning now to FIGS. 2A and 2B, in certain embodiments Applicants' invention automatically corrects for a rotation or tilt of patient 202's head during a Hess or Lancaster Red-Green Test, wherein head rotation causes actual vertical plane 206' to deviate from the nominal vertical plane 206 by an angle θ 208 with respect to screen 204, and/or wherein a head tilt upwardly or downwardly causes actual horizontal plane 210' to deviate from a nominal horizontal plane 210 by an angle Φ 212. The nominal horizontal plane 210 comprises an imaginary transverse plane passing through the patient's eyes. As will be appreciated by a person of ordinary skill in the art, Applicants' ability to correct for such head rotation and/or head tilt eliminates the need for head stabilization device 502. Therefore, in certain embodiments, a head stabilization device, such as head stabilization device 502, is not used. In certain embodiments, a head stabilization device, such as, by way of example and not limitation, a head/chin rest, is used with Applicant's invention, thereby minimizing the corrections needed to be applied.

Additionally, Applicants' method records both vertical and horizontal deviations in the locations of patient-directed green light 310 (FIGS. 3 and 5A) and each fixation point 312(n) (FIGS. 3 and 5A) synchronously with the patient's verification of light 310 position. Such recordation further eliminates the need for examiner 504 (FIG. 3) to be present during the examination.

Figure 3:
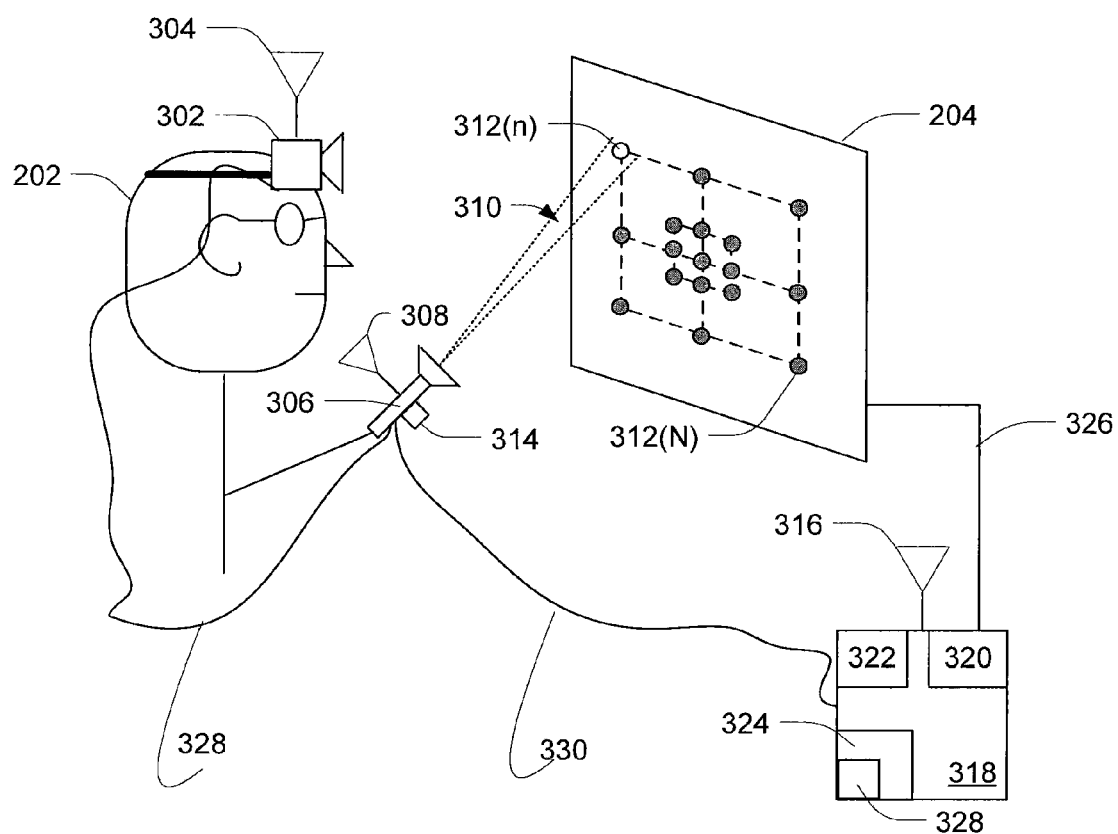
FIG. 3 is a block diagram illustrating an embodiment of a patient performing a Hess Screen Test according to the Applicants' invention.

FIG. 3 illustrates an embodiment of Applicant's apparatus and method to implement a Hess or Lancaster Red-Green test. Patient 202 is shown facing screen 204. In the illustrated embodiment of FIG. 3, screen 204 is shown as comprising (N) fixation points 312, each comprising a red light-emitting source. In certain embodiments, fixation points 312 are circular. In certain embodiments, fixation points 312 are linear. In certain embodiments, both linear and circular fixation points are used. In certain embodiments, screen 204 is electronic. In such embodiments, screen 204 may be a light emitting diode (LED) display.

In certain embodiments, screen 204 is surrounded by a shield which blocks ambient light. In such embodiments, the shield may be a box. In such embodiments the shield may be a curtain. In such embodiments, the shield may be large enough to surround at least the patient's head. In such embodiments, the shield may be large enough to surround the patient's head and torso. In certain embodiments, the screen is located in a dark room such that when the test is being performed there is no ambient light.

In certain embodiments, screen 204 is calibrated based on the ambient lighting. In such embodiments, screen 204 may be self-calibrating. In such an embodiment, screen 204 may calibrate based on the ambient light conditions before the start of each test. In such embodiments, the intensity of the screen 204 may be calibrated. In such embodiments, the color displayed on screen 204 may be calibrated.

In certain embodiments, screen 204 is portable. In such embodiments, screen 204 may be part of a portable container, wherein screen 204 is battery powered. In such embodiments, screen 204 may be calibrated based on the strength of the battery. In certain embodiments, screen 204, where portable, comprises a projector, wherein the projector is used to project fixation points 312 onto a wall or other surface. In such embodiments the projector may calibrate color scales, intensities, and other variations to take into effect wall color, surface textures, planarity of the surface, and other surface variations. In certain embodiments, portable screen 204 is part of an integrated embedded device, such as a laptop, tablet, or panel PC. In certain embodiments, screen 204, where portable, weighs less than one-hundred (100) pounds.

Fixation points 312 are located along lines extending outwardly from center point 330 in (N) diagnostic positions of gaze at fifteen degrees (15°), and in (N) diagnostic positions of gaze at thirty degrees (30°). In certain embodiments, (N) equals two (2). In certain embodiments, (N) equals nine (9). In certain embodiments, Applicants' method utilizes less than a total number of fixation points 312 on screen 204. By way of example and not limitation, two (2) fixation points 312 may be used for diagnosing a change in the ocular motor function of a patient. Alternatively, four (4) or more fixation points 312 may be used to diagnose a muscle palsy.

As described hereinabove, patient 202 wears a pair of glasses having one red lens and one green lens to force the dissociation of patient 202's eyes. Patient 202 then attempts, using light-emitting device 306 which emits green light 310, to illuminate seriatim each of the fixation points 312(n) as that fixation point is activated. In certain embodiments, light-emitting device 306 is a flashlight having a colored lens. In other embodiments, light-emitting device 306 is a pen light. In other embodiments, light-emitting device 306 is any other light source capable of emitting a green light and being directed by patient 202.

In certain embodiments, screen 204 is in communication with computing device 318 via communication link 326. In certain embodiments, computing device 318 controls the activation and deactivation of fixation points 312.

In the illustrated embodiment of FIG. 3, light-emitting device 306 includes trigger 314 and wireless communication interface 308. Patient 202 engages trigger 314 when the patient perceives that green light 310 is centered on an illuminated fixation point 312(n). In certain embodiments, light-emitting device 306, synchronously with activation of trigger 314, provides a signal to camera 302, wherein camera 302 is disposed atop patient 202's head. In certain embodiments, camera 302 is situated elsewhere. In certain embodiments, light-emitting device 306, synchronously with activation of trigger 314, provides a wireless signal to camera 302. In certain embodiments, light-emitting device 306, synchronously with activation of trigger 314, provides a wireless signal to wireless communication interface 316 of computing device 318.

In certain embodiments, light-emitting device 306 communicates wirelessly both with camera 302 and computing device 318. In certain embodiments, light-emitting device 306 communicates with camera 302 via a communication link 328, and with computing device 318 via a communication link 330.

In certain embodiments, trigger 314 is a button. In certain embodiments, trigger 314 is a finger trigger. In yet other embodiments, trigger 314 is a switch.

When activated, trigger 314 causes light-emitting device 306 to send an activation signal via wireless communication interface 308 to camera 302. Synchronously upon receipt of an activation signal, camera 302 records and stores an image of screen 204. In embodiments where camera 302 is not disposed atop patient 202's head, camera 302 may record an image of patient 202's head relative to a background reference. In other such embodiments, camera 302 may record an image of patient 202's head relative to screen 204.

In certain embodiments, camera 302 is a charge-coupled device (CCD). In other embodiments, camera 302 is an avalanche photodiode (ADP). In yet other embodiments, camera 302 is any photodetector capable of transforming a light pattern into an electronic charge pattern.

Camera 302 provides the recorded image via wireless communication interface 304 to wireless communication interface 316 of computing device 318. In certain embodiments, computing device 318 is selected from the group consisting of an application server, a web server, a work station, a host computer, or other like device from which information can be stored and/or processed. In certain embodiments, computing device 318 is interconnected to other computing devices using a data communication fabric via Small Computer Systems Interface ("SCSI") protocol running over a Fibre Channel ("FC") physical layer. In certain embodiments, the data communication fabric comprises one or more data switches. In certain embodiments, the data communication fabric is a wide area network ("WAN"). In certain embodiments, the data communication fabric is a local area network ("LAN"). In other embodiments, the connections between computing device 318 and other computing devices comprise other protocols, such as Infiniband, Ethernet, or Internet SCSI ("iSCSI").

In the illustrated embodiment of FIG. 3, computing device 318 comprises an operating system 322, computer readable medium 324, and processor 320. In certain embodiments computer readable medium 324 includes instructions 328. In certain embodiments, operating system 322 is encoded in computer readable medium 324.

As those skilled in the art will appreciate, computing device 318 comprises additional elements and features not shown in FIG. 3.

In certain embodiments, computer readable medium 324 comprises a magnetic information storage medium, an optical information storage medium, an electronic information storage medium, and the like. By "magnetic storage medium," it is meant, for example, a device such as a hard disk drive, floppy disk drive, or magnetic tape. By "optical information storage medium," it is meant, for example, a Digital Versatile Disk ("DVD"), High-Definition DVD ("HD-DVD"), Blu-Ray Disk ("BD"), Magneto-Optical ("MO") disk, Phase-Change ("PC") disk, etc. By "electronic storage media" it is meant, for example, a device such as PROM, EPROM, EEPROM, Flash PROM, compactflash, smartmedia, and the like. In certain embodiments, memory 324 comprises a magnetic information storage medium, and optical information storage medium, an electronic information storage medium, and the like.

In addition to accurately recording the locations of green light 310 on screen 204 and an illuminated fixation point 312(n) at the instant in time that trigger 314 is activated, in certain embodiments, camera 302 also records any rotation or tilt of patient 202's head. Thus, by comparing each recorded image to a reference image of screen 204, horizontal deviation angle 208 (FIG. 2B) and vertical deviation angle 212 can be determined. In certain embodiments, the reference image is an image of screen 204 taken while patient 202 was wearing camera 302. In other embodiments, the reference image is one of the images captured by camera 302 during the examination. In yet other embodiments, the reference image is a stored image of screen 204.

In certain embodiments, camera 302 comprises an inclinometer. As those skilled in the art will appreciate, an inclinometer is an instrument for measuring angles of slope (or tilt), or inclination of an object with respect to gravity. In these embodiments, the inclinometer element of camera 302 determines a vertical deviation angle 212.

In certain embodiments, camera 302 further comprises an Inertial Navigation System ("INS") comprising motion sensors (accelerometers) to continuously calculate the position, orientation, and velocity (direction and speed of movement) of patient 202's head without the need for external references. In these embodiments, the INS element of camera 302 determines a horizontal deviation angle 208 and a vertical deviation angle 212.

In certain embodiments, computing device 318 utilizes data provided by camera 302 to calculate a horizontal deviation angle 208 and/or a vertical deviation angle 212. In certain embodiments, computing device 318 determines a horizontal deviation angle 208 and/or a vertical deviation angle 212 for each image recorded by camera 302. In certain embodiments, computing device 318 applies a horizontal deviation angle 208 and/or a vertical deviation angle for head rotation and/or head tilt.

In certain embodiments, computing device 318 superimposes all (N) recorded images to create an ocular motor functioning chart for each eye, such as ocular motor functioning charts 102, 104, 106, and 108 (FIG. 1). In certain embodiments, computing device 318, superimposes all (N) corrected images to create a corrected ocular motor functioning chart for each eye.

Figure 4A:
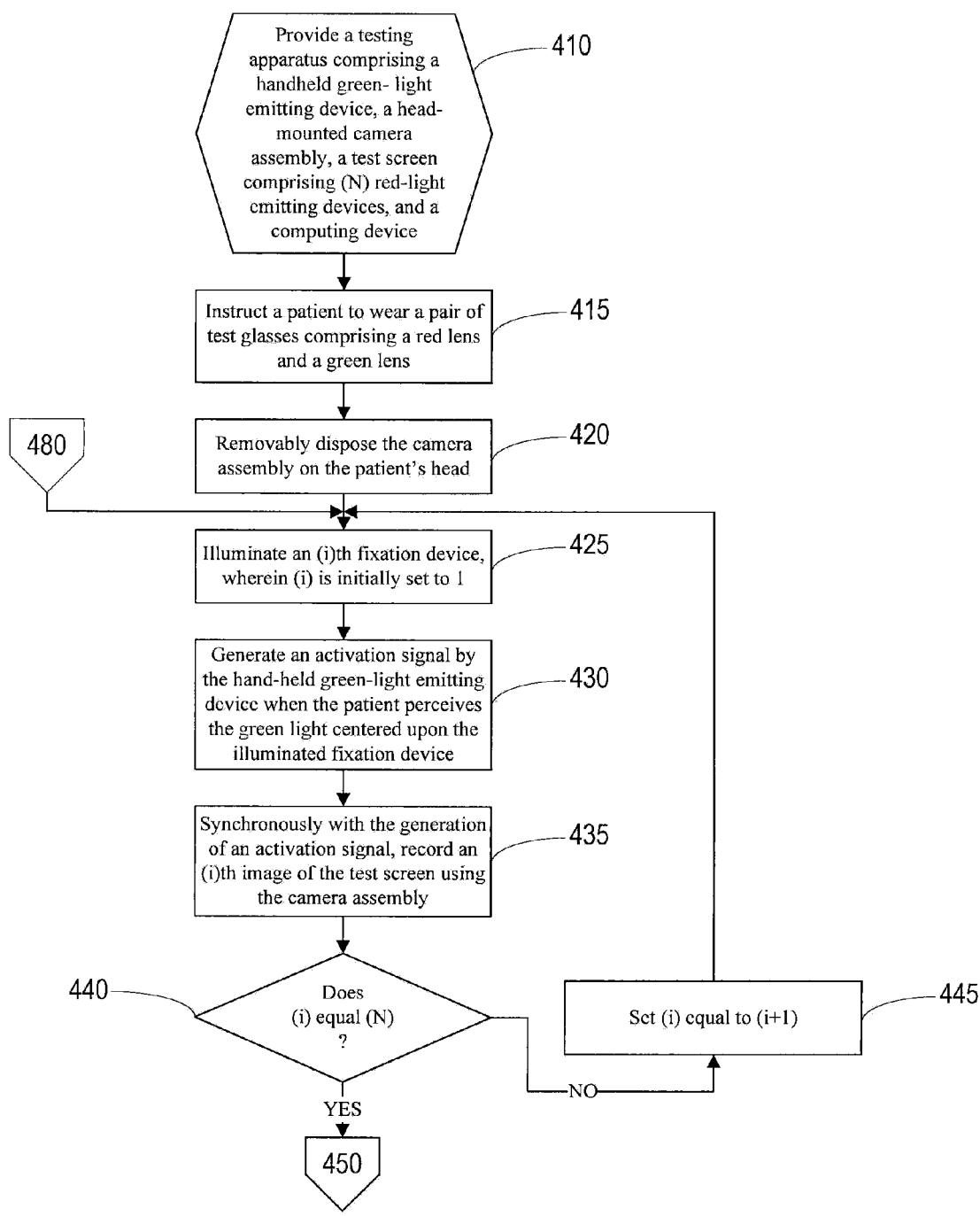
FIG. 4A is a flow chart summarizing the initial steps of an embodiment of Applicants' invention.
Figure 4B:
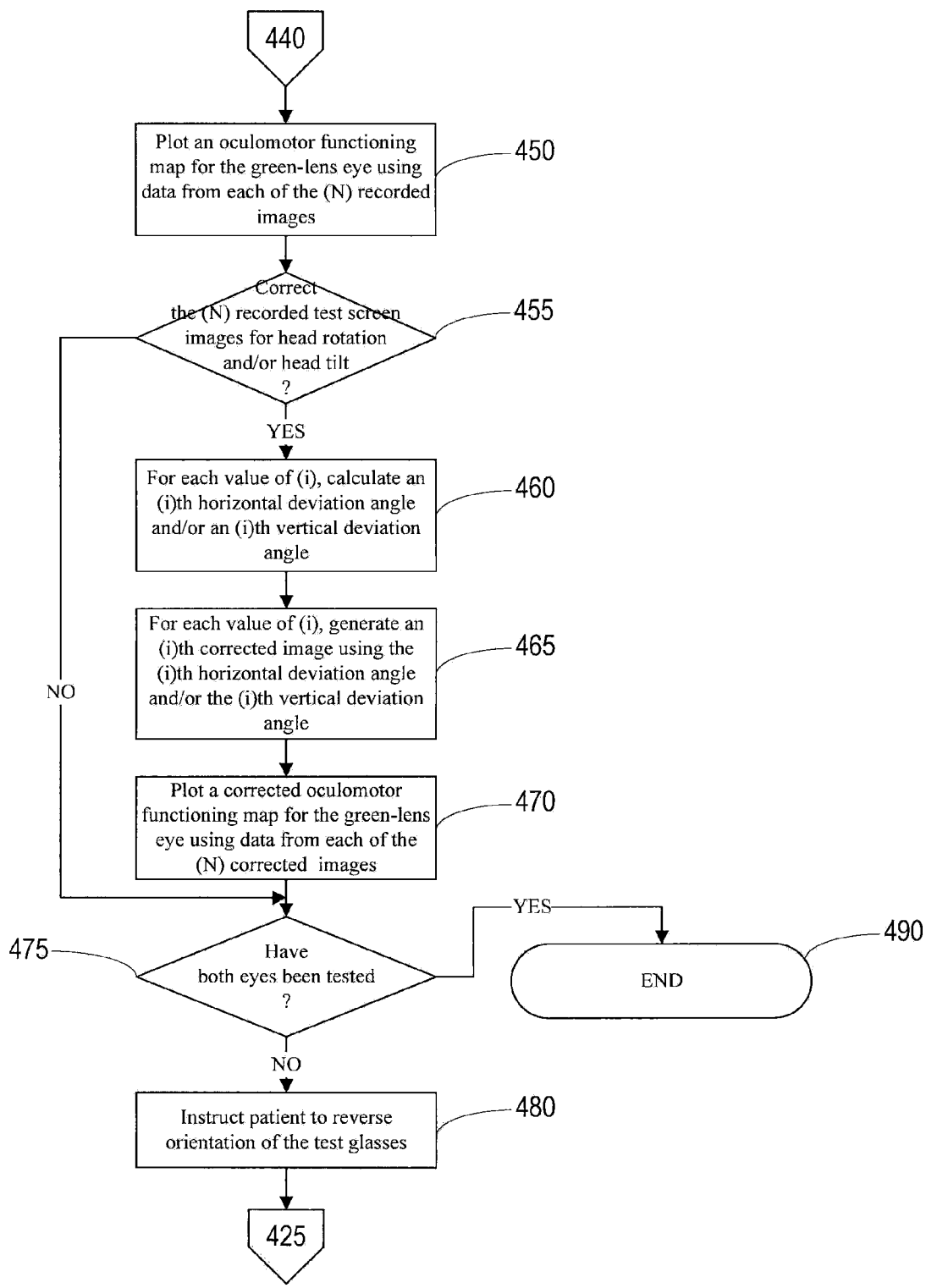
FIG. 4B is a flow chart summarizing additional steps of an embodiment of Applicants' invention.

FIGS. 4A and 4B summarize Applicants' method which utilizes Applicants' apparatus. Referring now to FIG. 4A, in block 410 the method provides a testing apparatus comprising a hand-held green-light emitting device, a head mounted camera assembly comprising (N) red colored fixation points, and a computing device. In certain embodiments, the test screen and hand-held green-light emitting device can be used for performing a Hess test. In certain embodiments, the test screen and the hand-held green-light emitting device can be used for performing a Lancaster Red-Green test. In certain embodiments, the test screen and the hand-held green-light emitting device can be used with either the Hess or the Lancaster Red-Green test.

In block 415, a patient is instructed to wear a pair of test glasses comprising a first lens having a first color and a second lens having a second color. In certain embodiments, the first or second color is red and the other color is green. In other embodiments, the first or second color is red and the other color is blue. In yet other embodiments, the first or second colors are any complementary colors.

In block 420, the method removeably disposes Applicants' camera assembly on the patient's head. In certain embodiments, the camera assembly of block 420 comprises a wireless communication interface. In certain embodiments, the camera assembly of block 420 comprises an inclinometer. In certain embodiments, the camera assembly of block 420 comprises an Inertial Navigation System.

In certain embodiments, in block 420 the method positions the patient's head such that the patient's cranial sagittal plane is perpendicular to the test screen of block 410, and such that the patient's cranial transverse plane is perpendicular to the test screen of block 410. In certain embodiments, a head stabilization device, such as, by way of example and not limitation, a head/chin rest, is used to position the patients head. In certain embodiments, in block 420 the method generates a reference inclinometer value and provides that reference inclinometer value to the computing device of block 410, and the computing device encodes that reference inclinometer value in a computer readable medium. In certain embodiments, in block 420 the method generates a reference INS data and provides that reference INS data to the computing device of block 410, and the computing device encodes that reference INS data in a computer readable medium.

In block 425, the method illuminates an (i)th fixation point, wherein (i) is initially set to 1, and wherein (i) is greater than or equal to 1 and less than or equal to (N). In certain embodiments, block 425 is performed by the computing device of block 410.

In certain embodiments, the fixation points are circular. In certain embodiments, the fixation points are rectangular. In certain embodiments, the fixation points can be either circular or rectangular. In certain embodiments, some of the fixation points are rectangular while some are circular.

In block 430, the patient attempts to center a green-colored light generated by the hand-held device of block 410 onto the illuminated fixation point of block 425. In certain embodiments, the hand-held device projects a green-colored, circularly-shaped light onto the test screen of block 410. In certain embodiments, the hand-held device projects a green-colored, rectangular-shaped light onto the test screen of block 410.

In embodiments wherein the method illuminates a circular fixation point, the hand-held device projects a circularly-shaped green light. In these embodiments, the patient attempts to center the circular green light onto the circular fixation point.

In embodiments wherein the method illuminates a rectangular fixation point, the hand-held device projects a rectangular-shaped green light. In these embodiments, the patient attempts to center the rectangular-shaped green light onto the rectangular fixation point.

Further in block 430, the hand-held green-light emitting device is caused to generate an activation signal when the patient perceives a green light emitted by the device centered upon the illuminated fixation point of block 425. In certain embodiments, the activation signal of block 430 is generated when the patient activates a trigger portion of the hand-held device of block 410. In these embodiments, when the patient perceives a green light centered upon the illuminated fixation point of block 425 the patient squeezes a trigger extending outwardly from the hand-held device, thereby causing the hand-held device to generate the activation signal of block 430.

In block 435, the method synchronously with the generation in block 430 of an activation signal, records an (i)th image of the test screen of block 410 using the camera assembly of block 410. In certain embodiments, the activation signal of block 430 comprises a wireless activation signal. In certain embodiments, the camera assembly of block 410 comprises a wireless communication interface, and that camera assembly wireless communication interface receives the wireless activation signal of block 430. Synchronously with the receipt of such a wireless activation signal, the camera assembly of block 410 records an (i)th image of the test screen of block 410.

In certain embodiments, a computing device, such as computing device 318 (FIG. 3), is used to calculate an (i)th horizontal deviation angle, and/or an (i)th vertical deviation angle, immediately after the (i)th image is recorded. In such an embodiment, the (i)th orientation angle may be used for real-time correction of the (i)th image. In other such embodiments, the (i)th horizontal deviation angle, and/or the (i)th vertical deviation angle is used to determine whether the patient will need to retake the test as it concerns the (i)th light-emitting device. In such an embodiment, the patient may be instructed to re-test the (i)th fixation point immediately. In such an embodiment, the (i)th horizontal deviation angle, and/or the (i)th vertical deviation angle, may be compared to threshold values, wherein only values outside the thresholds will require the patient to re-test the (i)th fixation point.

In block 440, the method determines if all (N) fixation points have been illuminated, i.e. if (i) equals (N). In certain embodiments, block 440 is performed by the computing device of block 410.

If the method determines in block 440 that fewer than all (N) fixation points have been illuminated, then the method transitions from block 440 to block 445 wherein the method sets (i) equal to (I+1). In certain embodiments, block 445 is performed by the computing device of block 410. The method transitions from block 445 to block 425 and continues as described herein.

If the method determines in block 440 that all (N) fixation points have been illuminated, then the method transitions from block 440 to block 450 wherein the method plots an ocular motor functioning map for the green-lens eye using data from each of the (N) recorded images. In certain embodiments, block 450 is performed by the computing device of block 410. In certain embodiments, in block 450 the computing device of block 410 is interconnected to the camera assembly of block 410 and the computing device downloads the (N) images recorded and stored in the iterations of block 435 (FIG. 4A) by the camera assembly of block 410. In certain embodiments, in block 450 the computing device of block 410 wirelessly downloads the (N) images recorded and stored in block 435 (FIG. 4A) by the camera assembly of block 410.

In block 455, the method determines whether to correct the (N) recorded images of block 435 for head rotation and/or head tilt. In certain embodiments, block 455 is performed by the computing device of block 410. In certain embodiments, block 455 is performed by an system operator.

If the method elects in block 455 not to correct the (N) recorded images of block 435 for head rotation and/or head tilt, then the method transitions from block 455 to block 475. Alternatively, if the method elects in block 455 to correct the (N) recorded images of block 435 for head rotation and/or head tilt, then the method transitions from block 455 to block 460 wherein the method, for each value of (i), calculates an (i)th horizontal deviation angle and/or an (i)th vertical deviation angle. In certain embodiments, block 460 is performed by the computing device of block 410.

In block 465, the method, for each value of (i), generates an (i)th correct image using the (i)th horizontal deviation angle of block 460 and/or using the (i)th vertical deviation angle of block 460. In certain embodiments, block 465 is performed by the computing device of block 410.

In block 470, the method plots a corrected ocular motor functioning map for the green-lens eye using data from each of the (N) corrected images of block 465.

In block 475, the method determines if both the patient's eyes have been tested. In certain embodiments, block 475 is performed by the computing device of block 410.

If the method determines in block 475 that both the patient's eyes have been tested, then the method transitions from block 475 to block 490 and ends. Alternatively, if the method determines in block 475 that both the patient's eyes have not been tested, then the method transitions from block 475 to block 480 wherein the patient is instructed to reverse the orientation of the test glasses of block 410, i.e. if the patient's left eye was previously the green-lens eye, then the patient repositions the test glasses such that the patient's right eye becomes the green-lens eye. The method transitions from block 480 to block 425 and continues as described herein.

In certain embodiments, Applicants' method described above in connection with FIGS. 4A and 4B is used to perform the Hess test. In certain embodiments, Applicants' method is used to perform the Lancaster Red-Green test. In certain embodiments, Applicants' method performs both the Hess test and the Lancaster Red-Green test in succession. In certain embodiments, Applicants' method begins by performing the Hess test and switches to the Lancaster Red-Green test upon indication that the patient has a torsional deficiency. In certain embodiments, Applicants' method begins by performing the Hess test and switches to the Lancaster Red-Green test upon some other indication. In certain embodiments, Applicants method begins by performing the Lancaster Red-Green test and switches to the Hess test.

In certain embodiments, individual processes described in connection with FIGS. 4A and 4B may be combined, eliminated, or reordered.

In certain embodiments, instructions, such as instructions 328 (FIG. 3), are encoded in computer readable medium, such as memory 324 (FIG. 3), wherein those instructions are executed by a processor, such as processor 320 (FIG. 3), to perform one or more of the blocks 425, 430, 435, 440, 445, 450, 455, 460, 465, and/or 470, recited in FIGS. 4A and 4B.

In yet other embodiments, the invention includes instructions residing in any other computer program product, where those instructions are executed by a computer external to, or internal to, computing device 318 (FIG. 3) to perform one or more of the blocks 425, 430, 435, 440, 445, 450, 455, 460, 465, and/or 470, recited in FIGS. 4A and 4B. In either case the instructions may be encoded in a computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compactflash, smartmedia, and the like.

While the preferred embodiments of the present invention have been illustrated in detail, it should be apparent that modifications and adaptations to those embodiments may occur to one skilled in the art without departing from the scope of the present invention.

What is claimed is:

1. A method of determining ocular motor function in a patient comprising:
instructing the patient to wear a pair of test glasses comprising a first lens having a first color and a second lens having a second color, wherein the first color and the second color differ;
activating, for each value of (i), an (i)th light-emitting device disposed in a screen comprising a total of (N) light emitting devices, wherein the illuminated (i)th light-emitting device emits a light comprising the first color, wherein (N) is greater than 1, and wherein (i) is greater than or equal to 1 and less than or equal to (N);

for each value of (i), synchronously capturing an (i)th screen image upon receiving a signal that the (i)th activated light-emitting device is illuminated by a light comprising the second color; and transforming (N) screen images into an ocular motor function map.

2. The method of claim 1, further comprising positioning the patient such that the cranial portion of the patient's sagittal plane is perpendicular to the screen.

3. The method of claim 1, further comprising, for each value of (i), determining an (i)th horizontal deviation angle.

4. The method of claim 3, further comprising, for each value of (i), determining an (i)th vertical deviation angle.

5. The method of claim 3, further comprising, for each values of (i), transforming an (i)th screen image into an (i)th corrected screen image using the (i)th horizontal deviation angle.

6. The method of claim 5, further comprising transforming (N) corrected screen images into a corrected ocular motor function map.

7. The method of claim 1, further comprising disposing a camera assembly on the head of the patient.

8. The method of claim 1, wherein (N) is equal to or greater than two, the method further comprising diagnosing a change in the ocular motor function of a patient.

9. The method of claim 1, wherein (N) is equal to or greater than four, the method further comprising diagnosing a muscle palsy.

10. A method of determining ocular motor function in a patient comprising:

instructing the patient to wear a pair of test glasses comprising a first lens having a first color and a second lens having a second color, wherein the first color and the second color differ;

projecting, for each value of (i), an (i)th fixation point comprising the first color onto a surface, wherein the (i)th fixation point is one of a (N) fixation points, wherein (N) is greater than 1, and wherein (i) is greater than or equal to 1 and less than or equal to (N).

for each value of (i), synchronously capturing an (i)th image upon receiving a signal that the (i)th activated light-emitting device is illuminated by a light comprising the second color; and transforming (N) images into an ocular motor function map.

11. The method of claim 10, further comprising calibrating said projection of the (i)th fixation point.

12. The method of claim 11, wherein said calibrating further comprises adjusting said projection of the (i)th fixation point based upon a color of the surface.

13. The method of claim 11, wherein said calibrating further comprises adjusting said projection of the (i)th fixation point based upon a texture of the surface.

14. The method of claim 11, wherein said calibrating further comprises adjusting said projection of the (i)th fixation point based upon a planarity of the surface.

15. The method of claim 11, wherein said projecting further comprises using a projector, wherein the projector comprises a battery, wherein said calibrating further comprises adjusting said projection of the (i)th fixation point based upon a charge of the battery.

* * * * *